United States Patent
Haugwitz et al.

(10) Patent No.: US 10,793,828 B2
(45) Date of Patent: Oct. 6, 2020

(54) PROTEIN ENRICHED MICROVESICLES AND METHODS OF MAKING AND USING THE SAME

(71) Applicant: Takara Bio USA, Inc., Mountain View, CA (US)

(72) Inventors: Michael Haugwitz, Belmont, CA (US); Thomas Patrick Quinn, Sunnyvale, CA (US); Andrew Alan Farmer, Los Altos, CA (US); Montserrat Morell Fernández, Menlo Park, CA (US)

(73) Assignee: Takara Bio USA, Inc., Mountain View, CA (US)

( * ) Notice: Subject to any disclaimer, the term of this patent is extended or adjusted under 35 U.S.C. 154(b) by 336 days.

(21) Appl. No.: 15/415,754

(22) Filed: Jan. 25, 2017

(65) Prior Publication Data
US 2017/0130197 A1    May 11, 2017

Related U.S. Application Data

(62) Division of application No. 14/278,714, filed on May 15, 2014, now Pat. No. 9,593,356.

(60) Provisional application No. 61/872,115, filed on Aug. 30, 2013, provisional application No. 61/833,880, filed on Jun. 11, 2013.

(51) Int. Cl.
| | |
|---|---|
| *C12N 5/071* | (2010.01) |
| *C07K 17/06* | (2006.01) |
| *C12P 21/02* | (2006.01) |
| *C07K 14/005* | (2006.01) |
| *C07K 14/435* | (2006.01) |
| *C12N 5/00* | (2006.01) |
| *C12N 9/06* | (2006.01) |
| *C12N 9/12* | (2006.01) |

(52) U.S. Cl.
CPC .......... *C12N 5/0602* (2013.01); *C07K 14/005* (2013.01); *C07K 14/43595* (2013.01); *C07K 17/06* (2013.01); *C12N 5/00* (2013.01); *C12N 9/003* (2013.01); *C12N 9/1241* (2013.01); *C12P 21/02* (2013.01); *C12Y 105/01003* (2013.01); *C07K 2319/00* (2013.01); *C07K 2319/70* (2013.01); *C12N 2501/998* (2013.01); *C12N 2760/00022* (2013.01); *C12N 2760/20222* (2013.01)

(58) Field of Classification Search
None
See application file for complete search history.

(56) References Cited

U.S. PATENT DOCUMENTS

| | | |
|---|---|---|
| 5,866,334 A | 2/1999 | Beutel |
| 5,871,753 A | 2/1999 | Crabtree et al. |
| 6,150,527 A | 11/2000 | Holt et al. |
| 2001/0044427 A1 | 11/2001 | Mazel et al. |
| 2007/0184060 A1 | 8/2007 | Bassaganya-Riera et al. |
| 2010/0047335 A1 | 2/2010 | Pedreno Egea et al. |
| 2010/0132071 A1 | 5/2010 | Hatzfeld et al. |
| 2012/0177574 A1 | 7/2012 | Gho |
| 2012/0322147 A1 | 12/2012 | Mangeot et al. |
| 2013/0034900 A1 | 2/2013 | Mangeot et al. |
| 2014/0080137 A1 | 3/2014 | Espinoza et al. |

FOREIGN PATENT DOCUMENTS

| | | |
|---|---|---|
| EP | 2589391 | 5/2013 |
| WO | WO1994018317 | 8/1994 |
| WO | WO1995002684 | 1/1995 |
| WO | WO1996012796 | 5/1996 |
| WO | WO1996013613 | 5/1996 |
| WO | WO1999041258 | 8/1999 |
| WO | WO2011002239 | 1/2011 |
| WO | WO2011058052 | 5/2011 |
| WO | WO2013/188522 | * 12/2013 |

OTHER PUBLICATIONS

B.Thaa et al. "Viruses as vesicular carriers of the viral genome: A functional module perspective", Biochimica et Biophysica Acta 1803: 507-519 (Year: 2010).*
B. Shen et al. "Protein Targeting to Exosomes/Microvesicles by Plasma Membrane Anchors", Journal of Biological Chemistry 286(16): 14383-14395 (Year: 2011).*
S.L. Noton et al. "Identification of the domains of the influenza A virus M1 matrix protein required for NP binding, oligomerization and incorporation into virions", Journal of General Virology 88: 2280-2290. (Year: 2007).*
Antonyak, et al. "Cancer cell-derived microvesicles induce transformation by transferring tissue ransglutaminase and fibronectin to recipient cells", Proc Nail Acad Sci, USA, 2011 ;108(12):4852-7.
Belshaw; et aL "Controlling programmed cell death with a cyclophilin-cyclosporin-based chemical inducer of dimerization", Chem Bioi (Sep. 1996), 3(9):731-738.
Belshaw; et aL "Controlling protein association and subcellular localization with a synthetic ligand that induces heterodimerization of proteins", PNAs (May 1996), 93(10):4604-4607.
Blau; et al. "{gamma}-Giobin gene expression in chemical inducer of dimerization (CID)-dependent multipotential cells established from human {beta}-globin locus yeast artificial chromosome ({beta}-YAC) transgenic mice", J Bioi Chern (Nov. 2005), 280{44):36642-36647.
Clontech, Switch on Protein-Protein Interactions, 2013, pp. 1-5.
Cutler; et al. "Abscisic acid: emergence of a core signaling network", Annu Rev Plant Bioi (2010), 61:651-679.

(Continued)

*Primary Examiner* — Rebecca E Prouty
(74) *Attorney, Agent, or Firm* — Bret E. Field; Bozicevic, Field & Francis LLP

(57) ABSTRACT

Protein enriched micro-vesicles and methods of making and using the same are provided. Aspects of the methods include maintaining a cell having a membrane-associated protein comprising a first dimerization domain and a target protein having a second dimerization domain under conditions sufficient to produce a micro-vesicle from the cell, wherein the micro-vesicle includes the target protein. Also provided are cells, reagents and kits that find use in making the micro-vesicles, as well as methods of using the micro-vesicles, e.g., in research and therapeutic applications.

16 Claims, 6 Drawing Sheets

(56) References Cited

OTHER PUBLICATIONS

Czlapinski; et al. "Conditional glycosylation in eukaryotic cells using a biocompatible chemical inducer of dimerization", JAm Chem Soc (Oct. 2008), 130(40):13186-13187.
De Graffenried; et al. "A small-molecule switch for Golgi sulfotransferases", PNAS (Nov. 2004), 101(48):16715-16720.
EP Communication dated Nov. 24, 2016 for European Application No. 14810531.5, 8 pages.
Finkelstein; et al. The *Arabidopsis* Abscisic Acid Response Gene ABI5 Encodes a Basic Leucine Zipper Transcription Factor, Plant Cell (Apr. 2000), 12(4):599-610.
Finkelstein; et al. The *Arabidopsis* abscisic acid response locus ABI4 encodes an APETALA 2 domain protein, Plant Cell (Jun. 1998), 10(6):1043-1054.
Fujii; et al. "In vitro reconstitution of an abscisic acid signalling pathway", Nature (Dec. 2009), 462(7273):660-664.
Giraudat; et al. "Abscisic acid signaling", Curr Opin Cell Bioi (Apr. 1995), 7(2):232-238, abstract only.
Harvey; et al. "Forced engagement of a RNA/protein complex by a chemical inducer of dimerization to modulate gene expression", PNAS (Feb. 2002), 99(4):1882-1887.
Hill; et al. "Abscisic Acid Structure-Activity Relationships in Barley Aleurone Layers and Protoplasts (Biological Activity of Optically Active, Oxygenated Abscisic Acid Analogs)", Plant Physiol (Jun. 1995), 108(2):573-579.
Liang; et al. "Engineering the ABA plant stress pathway for regulation of induced proximity", Sci Signal (Mar. 2011), 4(164):rs2.
Melcher; et al. "A gate-latch-lock mechanism for hormone signalling by abscisic acid receptors", Nature (Dec. 2009), 462(7273):602-608.
Miyazono; et al_ "Structural basis of abscisic acid signalling", Nature (Dec. 2009), 462(7273):609-614.
Nishimura; et al. "PYR1PYL/RCAR family members are major in-vivo ABI1 protein phosphatase 2C-interacting proteins in *Arabidopsis*", Plant J (Jan. 2010), 61(2):290-299.
Nishimura; et al. "Structural mechanism of abscisic acid binding and signaling by dimeric PYR1", Science (Dec. 2009), 326(5958):1373-1379.
Oritani; et al. "A Novel Abscisic Acid Analog, (+)-(2Z, 4E)-5-(1', 4'-Dihydroxy-6', 6'-dimethyl-2'-methylenecyclohexyl)-3-methyl-2,4-pentadienoic Acid, from Cercospora cruenta", (1984), 48(6):1677-1678.
Park; et al_ "Abscisic acid inhibits type 2C protein phosphatases via the PYRIPYL family of START proteins", Science (May 2009), 324(5930):1068-1071.
Patury; et al_ "Conditional nuclear import and export of yeast proteins using a chemical inducer of dimerization", Cell Biochem Biophys (2009), 53(3):127-134.
Santiago; et al. "The abscisic acid receptor PYR1 in complex with abscisic acid", Nature (Dec. 2009), 462(7273):665-668.
Sestelo; et al. "Design and synthesis of a 1 alpha,25-dihydroxyvitamin D3 dimer as a potential chemical inducer of vitamin D receptor dimerization", Org Letter (Oct. 1999), 1(7):1005-1007.
Shibata; et al. "Crystallization of the plant hormone receptors PYL9/RCAR1, PYL5/RCAR8 and PYR1/RCAR11 in the presence of (+)-abscisic acid", Acta Crystallogr Sect F Struct Bioi Cryst Commun (Apr. 2010), 66(Pt 4):456-459.
Stillwell; et al. "Abscisic acid enhances aggregation and fusion of phospholipid vesicles", Biochem Biophys Res Commun (Oct. 1988), 156(1):511-516.
Szostkiewicz; et al. "Closely related receptor complexes differ in their ABA selectivity and sensitivity", Plant J (Jan. 2010), 61(1):25-35.
Umezawa; et al. "Type 2C protein phosphatases directly regulate abscisic acid-activated protein kinases in *Arabidopsis*", PNAS (Oct. 2009), 106(41):17588-17593.
Walker-Simmons; et al. "Monoclonal antibody recognition of abscisic Acid analogs", Plant Physiol (Jan. 1991), 95{1}:46-51.
Yin; et al. "Structural insights into the mechanism of abscisic acid signaling by PYL proteins", Nat Struct Mol Bioi (Dec. 2009), 16(12):1230-1236.
Liang; et al., "Supplementary Materials for Engineering the ABA Plant Stress Pathway for Regulation of Induced Proximity", Science Signaling (Mar. 15, 2011), 4, rs2.
Mangeot; et al. "Protein transfer into human cells by VSV-G-induced nanovesicles", Mol. Ther_ (Sep. 2011) 19 {9}, 1656-1666.
Molina, et al. "The Ras/Raf/MAPK pathway", J Thorac Oncol. Jan. 2006;1(1):7-9.

* cited by examiner

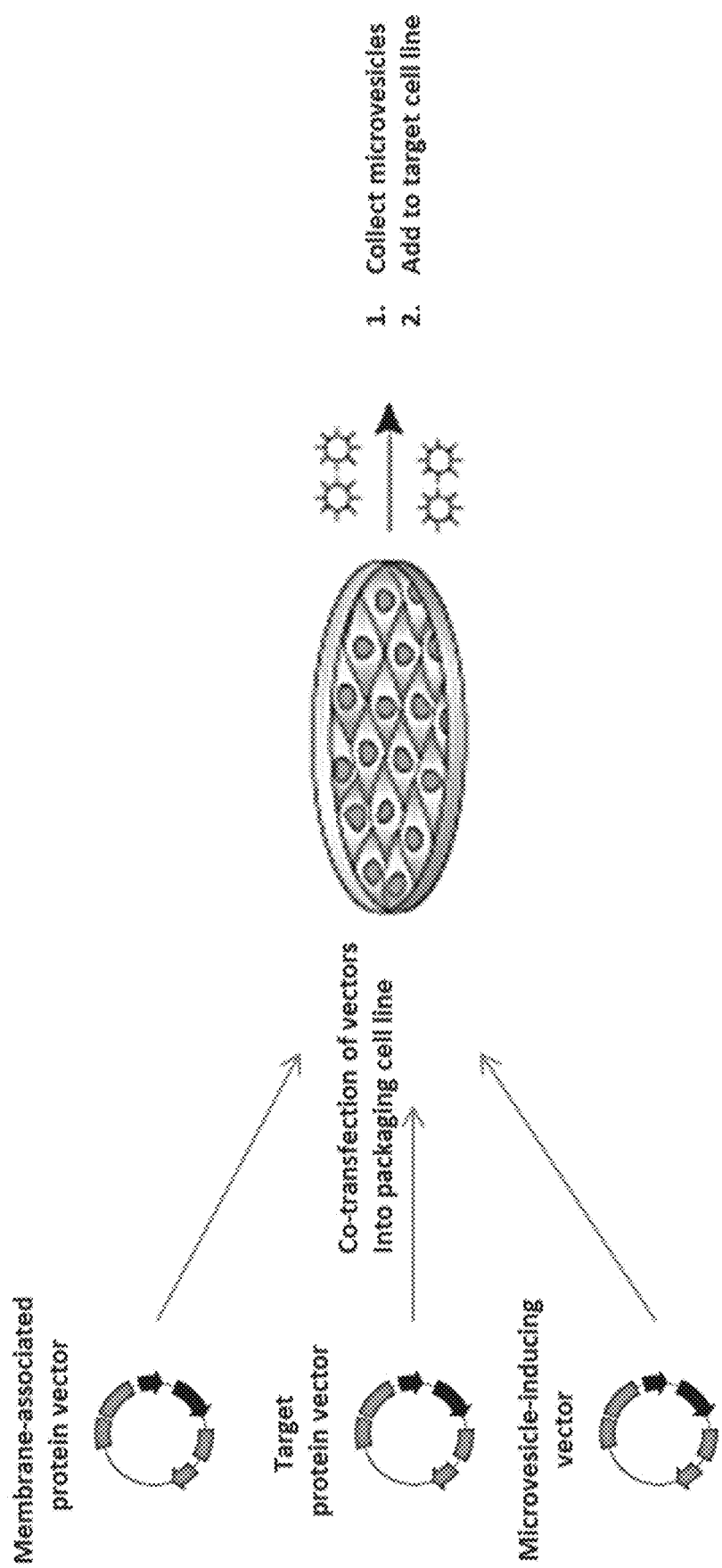

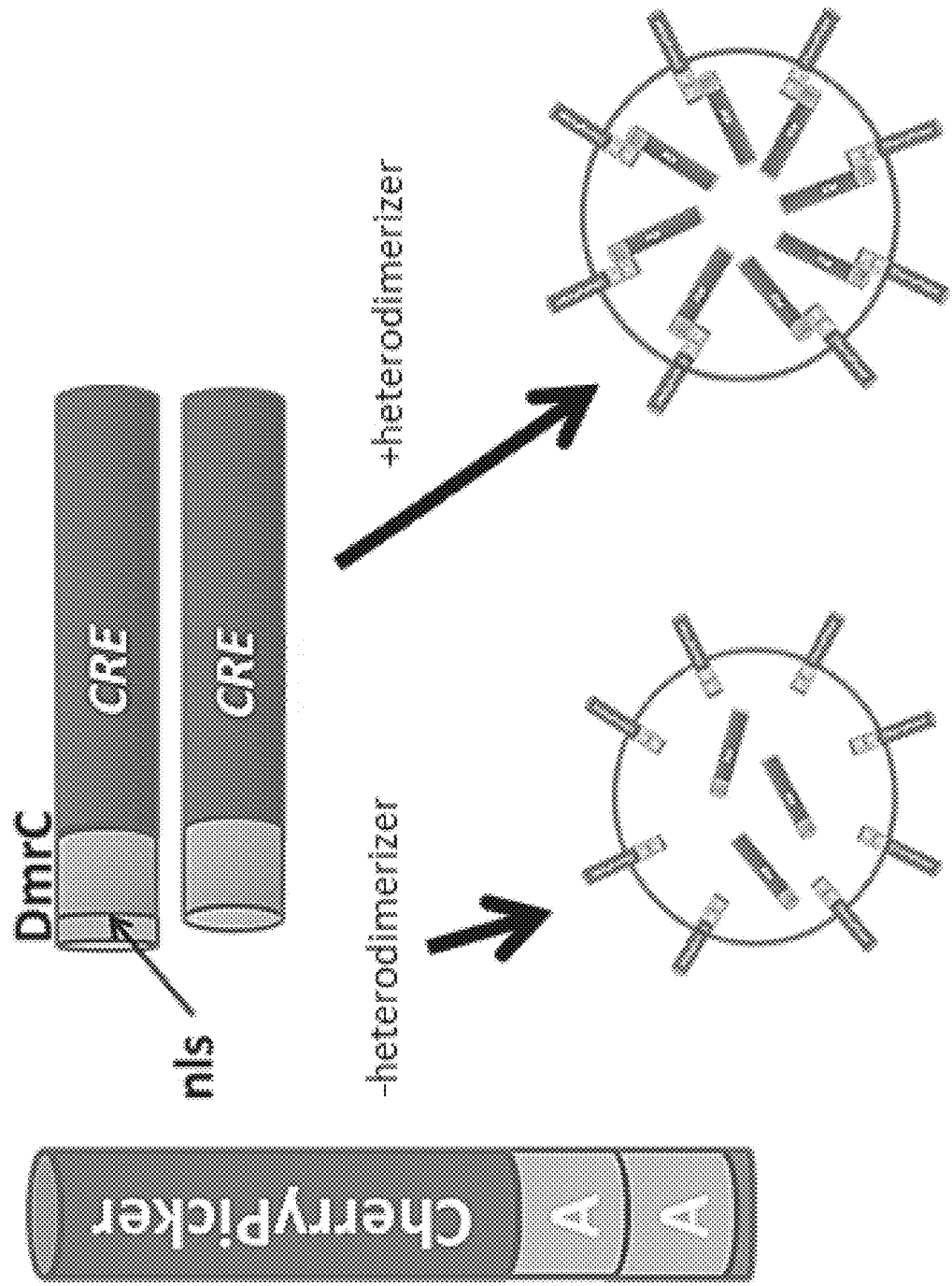

PROTEIN ENRICHED MICROVESICLES AND METHODS OF MAKING AND USING THE SAME

CROSS REFERENCE TO RELATED APPLICATIONS

Pursuant to 35 U.S.C. § 119 (e), this application claims priority to the filing date of the U.S. Provisional Patent Application Ser. No. 61/872,115, filed Aug. 30, 2013 and U.S. Provisional Patent Application Ser. No. 61/833,880, filed Jun. 11, 2013; the disclosure of which is herein incorporated by reference.

INTRODUCTION

Cell modification finds use in a variety of different applications, including research, diagnostic and therapeutic applications. Cell modification may be achieved using a number of different approaches, including the introduction of exogenous nucleic acids and/or proteins into a cell.

Protein delivery, which is known in the art as protein transduction, is the process by which a peptide or protein motif is delivered across the plasma membrane into the cell. Protein delivery methods include micro-injection and electroporation. Protein delivery methods also include: transfection by forming complexes with lipid-based reagents; transfection by forming complexes with polymer or peptide based reagents; direct addition through inclusion of a peptide transduction domain (PTD) to the protein of interest; virus like particle mediated introduction; and exosome mediated protein introduction.

One drawback of the current methods of protein delivery is the requirement to produce a stock of purified protein for transfection into the desired target cell. Standard methods for the production of recombinant protein can present issues with solubility, yield, correct folding and post-translational modifications. These methods also do not allow for the delivery of recombinant membrane proteins. Many of these factors are important because they directly relate to the activity of the protein to be transfected. The activity of the protein has the highest priority for direct delivery so that the delivered protein will exert an effect on a cell.

Another drawback to the current methods lies in the delivery itself. Both the lipid and polymer/peptide based transfection methods have issues with protein specific packaging efficiency due to unfavorable charge differences as well as inefficient delivery and toxicity. Electroporation also has been shown to have issues with toxicity, high level of inconsistency and a lack of control over the protein amount delivered. Inclusion of a PTD is known to cause aggregation and precipitation which can adversely affect delivery efficiency. Lastly, delivery of proteins in virus like particles (VLPs) requires that immune response-generating viral capsid proteins are used for packaging.

SUMMARY

Protein enriched micro-vesicles and methods of making and using the same are provided. Aspects of the methods include maintaining a cell having a membrane-associated protein comprising a first dimerization domain and a target protein having a second dimerization domain under conditions sufficient to produce a micro-vesicle from the cell, wherein the micro-vesicle includes the target protein. Also provided are cells, reagents and kits that find use in making the micro-vesicles, as well as methods of using the micro-vesicles, e.g., in research and therapeutic applications.

BRIEF DESCRIPTION OF THE FIGURES

FIG. 1 provides a schematic of the preparation and use micro-vesicles as described in the Experimental Section, below.

FIGS. 2A to 2D illustrate various aspects and provide results of an embodiment of the invention in which CRE recombinase micro-vesicles are produced.

DETAILED DESCRIPTION

Figure 2B:
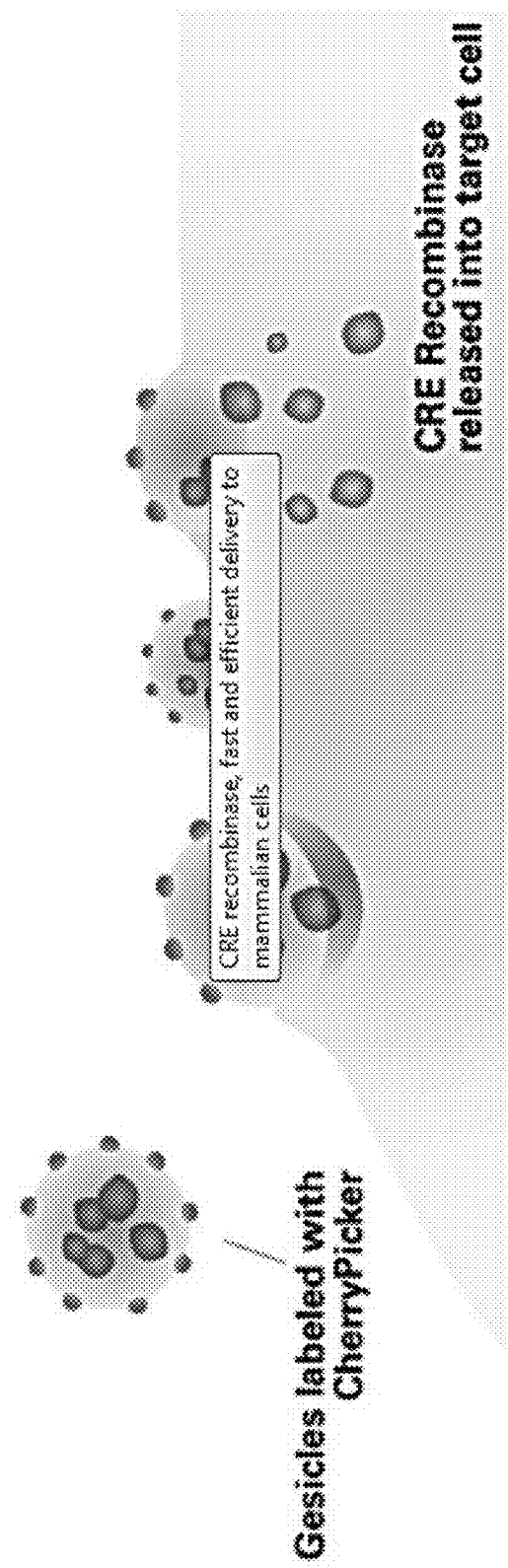

Protein enriched micro-vesicles and methods of making and using the same are provided. Aspects of the methods include maintaining a cell having a membrane-associated protein comprising a first dimerization domain and a target protein having a second dimerization domain under conditions sufficient to produce a micro-vesicle from the cell, wherein the micro-vesicle includes the target protein. Also provided are cells, reagents and kits that find use in making the micro-vesicles, as well as methods of using the micro-vesicles, e.g., in research and therapeutic applications.

Before the present invention is described in greater detail, it is to be understood that this invention is not limited to particular embodiments described, as such may, of course, vary. The invention encompasses various alternatives, modifications, and equivalents, as will be appreciated by those of skill in the art. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

Any publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Methods of Preparing Protein Enriched Micro-Vesicles

As summarized above, aspects of the invention include methods of producing protein-enriched micro-vesicles. By "protein-enriched micro-vesicle" is meant a fusogenic structure that includes an amount of one or more target proteins in a lipid bilayer envelope. As used herein, the term "fusogenic" refers to the property of the micro-vesicle which provides for the fusion of the membrane of the micro-vesicles to the membrane of the target cell. As the micro-vesicles are fusogenic, they are capable of fusion with the lipid bilayer membrane of a target cell to deliver their contents, including the target protein(s), into the cell. Before describing the protein-enriched micro-vesicles further, methods for their production are now reviewed in greater detail.

As summarized above, aspects of the methods include maintaining a micro-vesicle producing cell under conditions sufficient to produce a micro-vesicle from the cell, where the micro-vesicle includes one or more target proteins. The micro-vesicle producing cell has a membrane-associated protein that includes a first dimerization domain and a target protein that includes a second dimerization domain.

Membrane-Associated Protein that Includes a First Dimerization Domain

Cells employed in methods of making micro-vesicles include a membrane-associated protein having a first dimerization domain. The cell may include any convenient membrane-associated protein that includes a first dimerization domain. A membrane-associated protein is a protein that is capable of stably associating with, e.g., via a binding interaction, the membrane of a micro-vesicle, where the membrane-associated protein, when associated with a micro-vesicle membrane, may be configured so that the dimerization domain contacts the cytosol of the micro-vesicle. Membrane-associated proteins may vary in size, ranging in some instances from 5 kDa to 250 kDa, such as 10 kDa to 100 kDa and including 12 kDa to 50 kDa.

The membrane-associated protein may be modified to include a single dimerization domain or two or more dimerization domains (e.g., as described in greater detail below). In some cases, two or more membrane-associated proteins may be included in the subject cells and micro-vesicles. Each of the two or more membrane-associated proteins may independently include a dimerization domain for forming a dimerized complex with a target protein.

Membrane-associated proteins of interest include, but are not limited to, any protein having a domain that stably associates, e.g., binds to, integrates into, etc., a cell membrane (i.e., a membrane-association domain), where such domains may include myristoylated domains, farnesylated domains, transmembrane domains, and the like. Specific membrane-associated proteins of interest include, but are not limited to: myristoylated proteins, e.g., p60 v-src and the like; farnesylated proteins, e.g., Ras, Rheb and CENP-E,F, proteins binding specific lipid bilayer components e.g. AnnexinV, by binding to phosphatidyl-serine, a lipid component of the cell membrane bilayer and the like; membrane anchor proteins; transmembrane proteins, e.g., transferrin receptors and portions thereof; viral membrane fusion proteins, e.g., as described below, VSV-G, and the like.

Membrane-associated proteins of interest, in addition to including a membrane-association domain, also include a first dimerization domain. The first dimerization domain may vary widely, and may be a domain that directly binds to a second dimerization domain of a target protein or binds to a second dimerization domain via a dimerization mediator, e.g., as described in greater detail below. A given membrane-associated protein may include a single type of a given domain (e.g., dimerization domain, membrane associated domain, etc.) or multiple copies of a given domain, e.g., 2 or more, 3 or more, etc.; and/or multiple different dimerization domains, as desired. Additional domains may be present in a given membrane associated protein molecule, e.g., linker domains, detection domains (e.g., fluorescent proteins, other enzymatic reporters such as Luciferase and the like), etc., as desired. In a given membrane associated protein, the membrane association domain and dimerization domain(s) may be heterologous to each other, such that they are not naturally associated with each other. As such, the membrane associated protein of such embodiments is not a naturally occurring protein.

The cell may include a single membrane-associated protein or two or more distinct membrane-associated proteins, e.g., where two or more distinct target proteins are desired to be packaged into a micro-vesicle. As such, a micro-vesicle producing cell according to aspects of the invention may include a single membrane-associated protein or two or more different membrane-associated proteins of differing sequence, e.g., 3 or more, 4 or more 5 or more, etc., where in some instances the number of distinct membrane-associated proteins of differing sequence ranges from 1 to 10, such as 1 to 5, including 1 to 4.

Target Protein

As used herein, a target protein (i.e., protein of interest or POI) may be any polypeptide that is desired to be transferred into a cell. Target proteins may vary in size, ranging in some instances from 5 kDa to 250 kDa, such as 10 kDa to 100 kDa and including 12 kDa to 50 kDa. Target proteins of interest include, but are not limited to, nuclear proteins, transcriptional regulators, DNA binding and/or modifying enzymes, RNA binding and/or modifying enzymes, protein modifying enzymes, fluorescent proteins, cell cycle control proteins, kinases, structural proteins, signaling proteins, apoptotic proteins, translation regulators, peptide antigens, cytosolic proteins and the like. Specific target proteins of interest include, but are not limited to, those target proteins listed in the Utility section, below.

In some instances, the target protein (s) is an endogenous protein. In some instances, the target protein is a heterologous protein. As used herein, the term "heterologous" means that the protein is not expressed from a gene naturally found in the genome of the cell used to produce the micro-vesicle. The target protein may also be a mutant of the wild-type protein, such as a deletion mutant or a point mutant and may show a gain of function or loss of function for example a dominant negative mutant of the wild-type protein. Target proteins may also be chimeras of one of more protein domains so as to generate a target protein of novel function—e.g., a Tet Transactivator, which is a fusion of a tet repressor domain and a transactivation domain to create a novel transcriptional regulator or proteins obtained via domain swapping etc. In certain embodiments, the target protein does not include any viral membrane fusion protein or any fragment of a viral membrane fusion protein or derivatives retaining fusogenic properties. Specific target proteins of interest are further described in the Utility Section, below.

The cell may include a single target protein or two or more distinct target proteins of differing sequence which are desired to be packaged into a micro-vesicle. As such, a micro-vesicle producing cell according to aspects of the invention may include a single target protein or two or more distinct target proteins of differing sequence, e.g., 3 or more, 4 or more 5 or more, etc., where in some instances the number of distinct target proteins ranges from 1 to 10, such as 1 to 5, including 1 to 4.

Target proteins according to the invention include a second dimerization domain. The second dimerization domain may vary widely, where the second dimerization domain is a domain that dimerizes (e.g., stably associates with, such as by non-covalent bonding interaction, either directly or through a mediator) with the first dimerization domain of the membrane associated protein, either directly or through a dimerization mediator, e.g., as described in greater detail below. A given target protein may include a single type of a given domain (e.g., dimerization domain) or multiple copies of a given domain, e.g., 2 or more, 3 or more, etc. Additional domains may be present in a given target protein molecule, e.g., linker domains, etc., as desired. In a given target protein, the protein domain and dimerization domain(s) may be heterologous to each other, such that they are not naturally associated with each other. As such, the target protein of such embodiments is not a naturally occurring protein.

Dimerization Domains

The dimerization domains of the membrane-associated and target proteins may vary, where these dimerization domains may be configured to bind directly to each other or through a dimerization mediator, e.g., as described in greater detail below. Since the membrane-associated and target protein each include both a membrane-associated domain or target protein domain, respectively, and a dimerization domain, they may be viewed as chimeric proteins or fusion proteins having at least two distinct heterologous domains which are stably associated with each other. By "heterologous", it is meant that the at least two distinct domains of these chimeric proteins do not naturally occur in the same molecule. As such, these chimeric proteins are composed of at least two distinct domains of different origin. As the two domains of these proteins are stably associated with each other, they do not dissociate from each other under cellular conditions, e.g., conditions at the surface of a cell, conditions inside of a cell, etc. In a given chimeric or fusion protein, the two domains may be associated with each other directly or via an amino acid linker, as desired. An amino acid linker may have any convenient amino acid sequence and length.

With respect to the dimerization domains, these domains are domains that participate in a binding event, either directly or via a dimerization mediator, where the binding event results in production of the desired multimeric, e.g., dimeric, complex of the membrane associated and target proteins. As such, the first and second dimerization domains are domains that participate in the binding complex that includes the membrane-associated protein and target protein. The first and second dimerization domains specifically bind to each other or to a dimerization mediator, as desired. The terms "specific binding," "specifically bind," and the like, refer to the ability of different domains, e.g., first dimerization domain, second dimerization domain, dimerization mediator, to preferentially bind to each other relative to other molecules or moieties in a cell. In certain embodiments, the affinity between these binding pairs when they are specifically bound to each other in a binding complex is characterized by a $K_D$ (dissociation constant) of $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, or $10^{-15}$ M or less (it is noted that these values can apply to other specific binding pair interactions mentioned elsewhere in this description, in certain embodiments).

As mentioned above, the first and second dimerization domains are domains that are capable of binding each other in a multimeric, e.g., dimeric, complex. As such, any two convenient polypeptide domains that are capable of forming a complex with each other may be selected for use as the first and second dimerization domains. The first and second dimerization domains may be included as part of the membrane-associated protein and the one or more target proteins, respectfully, using any convenient method. In some cases, the membrane-associated protein and/or the one or more target proteins are fusion proteins that have been engineered to include a dimerization domain. When present in a fusion protein, the dimerization domain may be separated from the membrane-associated protein and/or the target protein by a linking sequence. In other cases, the dimerization domain may be a natural domain contained within the membrane-associated protein and/or the one or more target proteins.

Any convenient set of dimerization domains may be employed. The first and second dimerization domains may be homodimeric, such that they are made up of the same sequence of amino acids, or heterodimeric, such that they are made up of differing sequences of amino acids. Dimerization domains may vary, where domains of interest include, but are not limited to: ligands of target biomolecules, such as ligands that specifically bind to particular proteins of interest (e.g., protein:protein interaction domains), such as SH2 domains, Paz domains, RING domains, transcriptional activator domains, DNA binding domains, enzyme catalytic domains, enzyme regulatory domains, enzyme subunits, domains for localization to a defined cellular location, recognition domains for the localization domain, the domains listed at: http://pawsonlab.m-shri.on.ca/index.php?option=com_content&task=view&id=30&Itemid=63/, etc.

Dimerization domains of interest include, but are not limited to, protein domains of the iDimerize inducible homodimer (e.g., DmrB) and heterodimer systems (e.g., DmrA and DmrC) and the iDimerize reverse dimerization system (e.g., DmrD) (see e.g., www.Clontech.com Cat. Nos. 635068, 635058, 635059, 635060, 635069, 635088, 635090 and 635055) (See Clackson et al. (1998) Redesigning an FKBP-ligand interface to generate chemical dimerizers with novel specificity. Proc. Natl. Acad. Sci. USA 95(18): 10437-10442; Crabtree, G. R. & Schreiber, S. L. (1996) Three-part inventions: intracellular signaling and induced proximity. Trends Biochem. Sci. 21(11): 418-422; Jin et al. (2000) In vivo selection using a cell-growth switch. Nat. Genet. 26(1): 64-66; Castellano et al. (1999) Inducible recruitment of Cdc42 or WASP to a cell-surface receptor triggers actin polymerization and filopodium formation. Curr. Biol. 9(7): 351-360; Crabtree et al. (1997) Proximity and orientation underlie signaling by the non-receptor tyrosine kinase ZAP70. Embo. J. 16(18): 5618-5628; Muthuswamy et al. (1999) Controlled dimerization of ErbB receptors provides evidence for differential signaling by homo- and heterodimers. Mol. Cell. Biol. 19(10): 6845-6857).

The first and second dimerization domains may be selected from DmrA and DmrC domains, DmrB domains, DmrD domains, dimerization domains of the dihydrofolate reductase system, dimerization domains of TAg and p53, and dimerization domains of SH2 and a phosphotyrosine-binding protein.

Also of interest as dimerization domains are transcription activation domains. Transcription activation domains of interest include, but are not limited to: Group H nuclear receptor member transcription activation domains, steroid/thyroid hormone nuclear receptor transcription activation domains, synthetic or chimeric transcription activation domains, polyglutamine transcription activation domains, basic or acidic amino acid transcription activation domains, a VP16 transcription activation domain, a GAL4 transcription activation domains, an NF-κB transcription activation domain, a BP64 transcription activation domain, a B42 acidic transcription activation domain (B42AD), a p65 transcription activation domain (p65AD), or an analog, combination, or modification thereof.

As mentioned above, the first and second dimerization domains may also bind to a dimerization mediator to produce the desired complexes of membrane-associated protein and target protein. In other words, a dimerization mediator may promote the complexation of the first and second dimerization domains, e.g., where both the first and second dimerization domains specifically bind to different regions of the dimerization mediator. Any convenient dimerization mediator may be employed. A dimerization mediator is a compound that induces proximity of the membrane associated and target proteins under intracellular conditions. By "induces proximity" is meant that two or more, such as three or more, including four or more, molecules are spatially associated with each other through a binding event mediated by the dimerization mediator compound. Spatial association is characterized by the presence of a binding complex that includes the dimerization mediator and the at least membrane associated and target protein molecules. In the binding complex, each member or component is bound to at least one other member of the complex. In this binding complex, binding amongst the various components may vary. For example, the dimerization mediator may mediate a direct binding event between domains of membrane associated and target protein molecules. The mediated binding event may be one that does not occur in the absence of the mediator, or one that occurs to a lesser extent in the absence of the mediator, such that the mediator results in enhanced dimer production as compared to control situations where the mediator is absent. For example, in the presence of the dimerization mediator, a first dimerization domain of a membrane associated protein may bind to a second dimerization domain of a target protein molecule. The dimerization mediator may simultaneously bind to domains of the membrane associated and target molecules, thereby producing the binding complex and desired spatial association. In some instances, the dimerization mediator induces proximity of the membrane associated and target protein molecules, where these molecules bind directly to each other in the presence of the dimerization mediator.

Any convenient compound that functions as a dimerization mediator may be employed. A wide variety of compounds, including both naturally occurring and synthetic substances, can be used as dimerization mediators. Applicable and readily observable or measurable criteria for selecting a dimerization mediator include: (A) the ligand is physiologically acceptable (i.e., lacks undue toxicity towards the cell or animal for which it is to be used); (B) it has a reasonable therapeutic dosage range; (C) it can cross the cellular and other membranes, as necessary (where in some instances it may be able to mediate dimerization from outside of the cell), and (D) binds to the target domains of the chimeric proteins for which it is designed with reasonable affinity for the desired application. A first desirable criterion is that the compound is relatively physiologically inert, but for its dimerization mediator activity. In some instances, the ligands will be non-peptide and non-nucleic acid.

Dimerization mediator compounds of interest include small molecules and are non-toxic. By small molecule is meant a molecule having a molecular weight of 5000 daltons or less, such as 2500 daltons or less, including 1000 daltons or less, e.g., 500 daltons or less. By non-toxic is meant that the inducers exhibit substantially no, if any, toxicity at concentrations of 1 g or more/kg body weight, such as 2.5 g or more/kg body weight, including 5 g or more/kg body weight.

One type of dimerization mediator of interest is a compound (as well as homo- and hetero-oligomers (e.g., dimers) thereof), that is capable of binding to an FKBP protein and/or to a cyclophilin protein. Such compounds include, but are not limited to: cyclosporin A, FK506, FK520, and rapamycin, and derivatives thereof. Many derivatives of such compounds are already known, including synthetic analogs of rapamycin, which can be adapted for use in the subject methods as desired.

In some embodiments, the dimerization mediator is a rapamycin analog (i.e., a rapalog). Any suitable rapalog may be modified for use as a dimerization mediator in the subject methods. As used herein, the term "rapalogs" refers to a class of compounds comprising the various analogs, homologs and derivatives of rapamycin and other compounds related structurally to rapamycin. Rapalogs include but are not limited to, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and elimination, derivatization or replacement of one or more substituents of the cyclohexyl ring or replacement of the cyclohexyl ring with a substituted or unsubstituted cyclopentyl ring. Rapalogs, as that term is used herein, do not include rapamycin itself, and in some instances do not contain an oxygen bridge between C1 and C30. Rapalogs that may be used as dimerization mediators in embodiments of the invention include, but are not limited to, those compounds described in: U.S. Pat. Nos. 7,067,526; and 7,196,192; the disclosures of which are herein incorporated by reference. Further illustrative examples of rapalogs are disclosed in the following documents: U.S. Pat. Nos. 6,693,189; 6,984,635, WO9641865, WO9710502, WO9418207, WO9304680, U.S. Pat. Nos. 5,527,907, 5,225,403, WO9641807, WO9410843, WO9214737, U.S. Pat. Nos. 5,484,799, 5,221,625, WO9635423, WO9409010, WO9205179, U.S. Pat. Nos. 5,457,194, 5,210,030, WO9603430, WO9404540, U.S. Pat. Nos. 5,604,234, 5,457,182, 5,208,241, WO9600282, WO9402485, U.S. Pat. Nos. 5,597,715, 5,362,735, 5,200,411, WO9516691, WO9402137, U.S. Pat. Nos. 5,583,139, 5,324,644, 5,198,421, WO9515328, WO9402136, U.S. Pat. Nos. 5,563,172, 5,318,895, 5,147,877, WO9507468, WO9325533, U.S. Pat. Nos. 5,561,228, 5,310,903, 5,140,018, WO9504738, WO9318043, U.S. Pat. Nos. 5,561,137, 5,310,901, 5,116,756, WO9504060, WO9313663, U.S. Pat. Nos. 5,541,193, 5,258,389, 5,109,112, WO9425022, WO9311130, U.S. Pat. Nos. 5,541,189, 5,252,732, 5,093,338, WO9421644, WO9310122, U.S. Pat. Nos. 5,534,632, 5,247,076, and 5,091,389, the disclosures of which are herein incorporated by reference.

Dimerization domains that may be incorporated into the membrane-associated and target proteins for use with such dimerization mediators may vary. In some instances, the dimerization domains may be selected from naturally occurring peptidyl-prolyl isomerase family proteins or derivatives, e.g., mutants (including point and deletion), thereof. Examples of domains of interest for these embodiments include, but are not limited to: FKBP, FRB, and the like.

FKBP dimerization domains may contain all or part of the peptide sequence of an FKBP domain. Of interest are those domains that are capable of binding to a corresponding dimerization mediator, e.g., a rapalog, with a Kd value of, e.g., 100 nM or less, such as about 10 nM or less, or even about 1 nM or less, as measured by direct binding measurement (e.g. fluorescence quenching), competition binding measurement (e.g. versus FK506), inhibition of FKBP enzyme activity (rotamase), or other assay methodology. The peptide sequence of a FKBP domain of interest may be modified to adjust the binding specificity of the domain for a dimerization mediator, e.g., by replacement, insertion or deletion of 25 or less, such as 20 or less, 15 or less, 10 or less, such as 5 or less, or 3 or less amino acid residues. A FRB domain of interest includes domains capable of binding to a complex of an FKBP protein and dimerization mediator, e.g., rapalog. The FRB fusion protein may bind to that complex with a Kd value of about 200 µM or less, such as about 10 µM or less, 2 µM or less, or even 1 µM or less, as measured by conventional methods. The FRB domain is of sufficient length and composition to maintain high affinity for a complex of the rapalog with the FKBP fusion protein.

Another type of dimerization mediator compound of interest is an alkenyl substituted cycloaliphatic (ASC) dimerization mediator compound. ASC dimerization mediator compounds include a cycloaliphatic ring substituted with an alkenyl group. In certain embodiments, the cycloaliphatic ring is further substituted with a hydroxyl and/or oxo group. In some cases, the carbon of the cycloaliphatic ring that is substituted with the alkenyl group is further substituted with a hydroxyl group. The cycloaliphatic ring system may be an analog of a cyclohex-2-enone ring system. In some embodiments, the ASC dimerization mediator compound includes a cyclohexene or a cyclohexane ring, such as is found in a cyclohexenone group (e.g. a cyclohex-2-enone), a cyclohexanone group, a hydroxy-cyclohexane group, a hydroxy-cyclohexene group (e.g., a cyclohex-2-enol group) or a methylenecyclohexane group (e.g. a 3-methylenecyclohexan-1-ol group); where the cycloaliphatic ring is substituted with an alkenyl group of about 2 to 20 carbons in length, that includes 1, 2, 3, 4, 5, 6, 7, 8, 9 or 10 unsaturated bonds. In certain embodiments, the alkenyl substituent includes a conjugated series of unsaturated bonds. In particular embodiments, the alkenyl substituent may be 4 carbons in length and include 2 conjugated double bonds. In another embodiment, the alkenyl substituent is conjugated to the cycloaliphatic ring system. Further details of such compounds are disclosed in WO/2011/163029; the disclosure of which is herein incorporated by reference.

Where the dimerization domain is an ASC inducer compound, such as abscisic acid, ASC binding dimerization domains of interest include, but are not limited to: the abscisic acid binding domains of the pyrabactin resistance (PYR)/PYR1-like (PYL)/regulatory component of ABA receptor (RCAR) family of intracellular proteins. The PYR/PYL/RCAR abscisic acid binding domains are those domains or regions of PYR/PYL/RCAR proteins, (e.g., pyrabactin resistance 1, PYR1-Like proteins, etc.) that specifically bind to abscisic acid. Accordingly, ASC inducer binding domains include a full length PYR1 or PYL protein (e.g., PYL1, PYL 2, PYL 3, PYL 4, PYL 5, PYL 6, PYL, PYL 8, PYL 9, PYL 10, PYL11, PYL12, PYL13), as well as portions or mutants thereof that bind to abscisic acid, e.g., amino acid residues 33-209 of PYL1 from *Arabidopsis thaliana*. Additional examples of suitable ASC binding dimerization domains include PP2C inducer domains. The PP2C inducer domains are those PYR/PYL binding domains found in group A type 2 C protein phosphatases (PP2Cs), where PP2Cs have PYL(+ABA) binding domains. Accordingly, ASC inducer binding domains include the full length PP2C proteins (e.g., ABI1), as well as portions or mutants thereof that bind to abscisic acid, e.g., amino acid residues 126-423 of ABI1 from *Arabidopsis thaliana*. In some instances, the PP2C ASC inducer domain is a phosphatase negative mutant, e.g., a mutant of PP2C that retains its ability to specifically bind to PYR/PYL (+ABA) and yet has reduced if not absent phosphatase activity.

Another type of dimerization mediator compound of interest is an N-oxalyl-pipecolyl or N-oxalyl-prolyl-type compound. N-oxalyl-pipecolyl and N-oxalyl-prolyl-type compounds include immunophilin multimerizing agents described in WO 1996/06097, the disclosure of which is herein incorporated by reference. Another type of dimerization mediator compound of interest is an oligonucleotide ligand containing compound. Oligonucleotide ligand containing compounds include multi-functional oligonucleotide ligands described in WO 1993/03052, the disclosure of which is herein incorporated by reference.

In some instances, the dimerization mediator is a modifiable dimerization mediator. In some instances, the dimerization mediator is modifiable (e.g., a MDM). A MDM is a compound that reversibly induces proximity of the membrane-associated protein and the target protein in a sample under suitable conditions, where proximity may be reversed by the application of a stimulus. Application of the stimulus to the sample modifies a modifiable group of the MDM, thereby changing the nature of the MDM such that the modified MDM is no longer capable of inducing or maintaining proximity of the membrane-associated protein and the target protein.

By "reversibly induces proximity" or "reverse the induction of proximity" is meant that the spatial association of membrane-associated protein and the target protein, mediated by a MDM, may be reversed upon application of a suitable stimulus (e.g., a photon, a chemical agent or an enzyme) that modifies the MDM. Application of a suitable stimulus results in dissociation of the membrane-associated protein and the target protein components of the dimeric complex. In some cases, the stimulus may be described as a modifying stimulus, e.g., a stimulus that results in modification of the modifiable group. In certain embodiments, application of a stimulus is not application of a competitive inhibitor of binding of the MDM to domains of the membrane-associated protein and target protein. In certain embodiments, application of a stimulus is not dilution of the sample.

Application of a suitable stimulus to the sample will modify the modifiable group to result in modification of the MDM, e.g., a change in the nature of the MDM molecule that alters its binding properties. In some embodiments, the modified MDM has significantly reduced affinity for the dimerization domains of the membrane-associated protein and/or the target protein, e.g., an affinity that is reduced by 2-fold or more, such as 3-fold or more, 4-fold or more, 5-fold or more, 10-fold or more, 30-fold or more, 50-fold or more, 100-fold or more, or even 1000-fold or more, as compared to the corresponding affinity of the unmodified MDM. In some embodiments, the Kd value of a MDM (e.g., a rapalog-derived or a ASC-derived MCIP), for a dimerization domain (e.g., a FKBP domain or a ASC binding domain) may be raised from about 10 nM or less (e.g., about 3 nM or less or about 1 nM or less) to about 20 nM or more, such as about 30 nM or more, about 40 nM or more, about 50 nM or more, about 100 nM or more, about 200 nM or more, about 500 nM or more, or even about 1 µM or more.

In some embodiments, the MDM includes a cleavable group where application of the stimulus cleaves the cleavable group. Application of the stimulus may produce two cleaved MDM products, where each product independently retains affinity for only one of the first and second dimerization domains. In some embodiments, the MDM includes a cleavable linker connecting a first binding moiety that specifically binds the first dimerization domain, and a second binding moiety that specifically binds the second dimerization domain, such that cleavage of the linker leads to dissociation of the membrane-associated protein and the target protein. In other embodiments, application of the stimulus produces a modified MDM where one of the first and second binding moieties is changed in nature such that it has significantly reduced affinity (e.g., as described herein) for a corresponding dimerization domain. In such cases, the binding affinity of the other binding moiety may be unaffected, or alternatively, it may also be significantly reduced (e.g., as described herein).

The MDM may include a first binding moiety (A) that specifically binds to a first dimerization domain and a second binding moiety (B) that specifically binds to a second dimerization domain, and a modifiable group (X). A MDM of the invention may be described by formula (I):

(I)

wherein A is a first binding moiety, B is a second binding moiety and X is a modifiable group. In certain embodiments, in formula (I), X may be a part of A or a part of B, or X may be connected to A and/or B via a linker. In some instances, the MDM specifically binds the first and second dimerization domains independently, e.g., formation of a ternary complex may occur via initial binding of the MDM to either the first or the second dimerization domain. In other instances, specific binding of the MDM to the second dimerization domain is dependent on prior formation of a MDM/first dimerization domain complex. In this context, by "dependent" is meant that the second target molecule has a higher affinity for the complex of MDM/first dimerization domain than it has for the MDM alone. In some embodiments, MDMs which form such ternary complexes include a first binding moiety (A) that specifically binds a first dimerization domain (e.g., a rapalog that specifically binds a FKBP domain, or an alkenyl substituted cycloaliphatic (ASC) inducer compound that specifically binds an PYL ASC binding domain), and the second binding moiety (B) that specifically binds a second dimerization domain (e.g., a rapalog that specifically binds a FRB domain, or an ASC inducer compound that specifically binds an ABI ASC binding domain) where binding of the second dimerization domain is dependent on the prior binding of A and the first dimerization domain. In certain cases, the complex of MDM/first dimerization domain specifically binds the second dimerization domain without direct contacts being formed between the MDM and the target protein. In such cases, the MDM mediates the binding of the membrane-associated protein and the target protein.

The modifiable group (X) may be included at any convenient position in the structure of an MDM. In some cases, the modifiable group (X) is part of the first binding moiety (A) or is part of the second binding moiety (B). In some cases, X may be included in that part of the structure which specifically binds the first dimerization domain (e.g., a FKBP domain or ASC binding domain), or alternatively, may be included in that part of the structure which specifically binds the second dimerization domain (e.g., a FRB domain or a ASC binding domain). In other cases, X may be separate from the binding moieties A and B. As such, X may be located at a position of the structure that is not involved in specific binding interactions with the first or second dimerization domains, e.g., in a linker that connects A and B.

Of interest as MDMs are the MCIPs and dimerization systems described in conjunction therewith as described in U.S. Provisional Patent Application No. 61/700,683 filed on Sep. 13, 2012, the disclosure of which is herein incorporated by reference.

Micro-Vesicle Inducer

As used herein, "micro-vesicle inducer" refers to an agent that promotes (i.e., enhances) the production of micro-vesicles from a cell. In some cases, the micro-vesicle inducer is a molecule that does not become part of the micro-vesicles, but where the presence of the micro-vesicle inducer results in the cell producing micro-vesicles. In other cases, the micro-vesicle inducer becomes part of the produced micro-vesicles. In some instances, the production of micro-vesicles can be accomplished through the overexpression of a micro-vesicle inducer within a mammalian cell. In certain cases, overexpression of a micro-vesicle inducer in a cell results in shedding of micro-vesicles into the medium surrounding the transfected cell.

The micro-vesicle inducer may be a protein, small molecule inducer, endogenous "cell-blebbing" e.g., during apoptosis, and the like. Protein micro-vesicle inducers include, but are not limited to: proteins that induce membrane budding, viral membrane fusion proteins, small molecule inducers of vesicle formation, etc.

In some cases, the micro-vesicle inducer is a protein that induces membrane budding such that the production of micro-vesicles is enhanced. As used herein, the expression "protein which induces membrane budding" refers to any protein that can promote the deformation of lipid bilayers and mediate the formation of vesicles. Any convenient cellular or viral proteins may be utilized to induce membrane budding. Cellular proteins of interest that induce membrane budding include, but are not limited to, proteolipid protein PLP1 (Trajkovic et al. 2008 Science, vol 319, p 1244-1247), clathrin adaptor complex AP1 (Camus et al., 2007. Mol Biol Cell vol 18, p 3193-3203), proteins modifying lipid properties such as fleippase, scramblase, proteins which facilitate secretion via a non-classical pathway such as TSAP6 (Yu et al. 2006 Cancer Res vol 66, p 4795-4801) and CHMP4C (Yu et al. 2009, FEBS J. vol 276, p 2201-2212). Viral proteins of interest that induce membrane budding include, but are not limited to, tetherin/CD317 antagonists such as the Vpu protein of HIV (Neil et al. 2008. Nature vol 451, p 425-4431) and various viral structural proteins such as retroviral GAG (Camus et al., 2007. Mol Biol Cell vol 18, p 3193-3203) and Ebola VP40 (Timmins et al., Virology 2001).

In some cases, the micro-vesicle inducer is a viral membrane fusion protein (e.g., viral fusion glycoprotein). The viral membrane fusion protein may be a class I viral membrane fusion protein such as the influenza-virus hemagglutinin, a class II viral membrane fusion protein or a class III viral membrane fusion protein (e.g., as described in Backovic et al., Curr. Opin. Struct. Biol. 2009, 19(2): 189-96; Courtney et al., Virology Journal 2008, 5: 28). In some embodiments, the viral membrane fusion protein is a class I viral membrane fusion protein. Class I viral membrane fusion proteins of interest include, but are not limited to, Baculovirus F proteins, F proteins of the nucleopolyhedrovirus (NPV) genera, such as Spodoptera exigua MNPV (SeMNPV) F protein and Lymantria dispar MNPV (LdMNPV) F protein. The micro-vesicle inducer may be a class III viral membrane fusion protein, where Class III viral membrane fusion proteins of interest include, but are not limited to, rhabdovirus G (such as the fusogenic protein G of the Vesicular Stomatatis Virus (VSV-G)), herpesvirus gB (such as the glycoprotein B of Herpes Simplex virus 1 (HSV-1 gB)), EBV gB, thogotovirus G, baculovirus gp 64 (such as Autographa California multiple NPV (AcMNPV) gp 64), and the Borna disease virus (BDV) glycoprotein (BDV G). In certain instances, the viral membrane fusion protein is VSV-G or baculovirus gp 64.

In certain embodiments, the micro-vesicle inducer is VSV-G, such as the VSV-G polypeptide as defined in GenBank AN: M35219.1, or any functional fragments or their functional derivatives retaining fusogenic properties. As used herein with respect to viral membrane fusion proteins, the term "fusogenic" refers to a viral protein that can induce the fusion of the membrane of the microvesicles to the plasma membrane of the target cell. VSV-G fusogenic polypeptides of interest include but are not limited to, those described in U.S. Pat. Nos. 7,323,337; 5,670,354; 5,512,421; 20100167377; and the like.

Also of interest are small molecule inducers of vesicle formation. Small molecule inducers of vesicle formation include, but are not limited to: Apoptosis inducer causing cell blebbing e.g. Staurosporin, and the like.

Where desired, a micro-vesicle inducer may be provided in the cell using any convenient protocol. For example, the cell may be configured to express the micro-vesicle inducer from a coding sequence in the cell, or a micro-vesicle inducer may be added to the cells using any convenient method. Methods of adding a micro-vesicle inducer to a cell include, but are not limited to, transfection or transduction of the cell with a construct encoding a micro-vesicle inducing protein, and contact of the cell with a chemical inducer (e.g., a small molecule), etc.

Micro-Vesicle Producing Cells

Any convenient cell capable of producing micro-vesicles may be utilized. In some instances, the cell is a eukaryotic cell. Cells of interest include eukaryotic cells, e.g., animal cells, where specific types of animal cells include, but are not limited to: insect, worm, avian or mammalian cells. Various mammalian cells may be used, including, by way of example, equine, bovine, ovine, canine, feline, murine, non-human primate and human cells. Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Hematopoietic cells of interest include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells, such as ES cells, epi-ES cells and induced pluripotent stem cells (iPS cells). Specific cells of interest include, but are not limited to: mammalian cells, e.g., HEK-293 and HEK-293T cells, COS7 cells, Hela cells, HT1080, 3T3 cells etc.; insect cells, e.g., High5 cells, Sf9 cells, Sf21 and the like. Additional cells of interest include, but are not limited to, those described in US Publication No. 20120322147, the disclosure of which cells are herein incorporated by reference.

As summarized above, the cells are ones that include a membrane-associated protein, a target protein and, where desired, a micro-vesicle inducer, e.g., as described in greater detail above. As such, the cells are cells that have been engineered to include the membrane-associated and target proteins. The protocol by which the cells are engineered to include the desired proteins may vary depending on one or more different considerations, such as the nature of the target cell, the nature of the molecules, etc. The cell may include expression constructs having coding sequences for the proteins under the control of a suitable promoter, where the promoter may be an inducible promoter or constitutively active. The coding sequences will vary depending on the particular nature of the protein encoded thereby, and will include at least a first domain that encodes the dimerization domains and a second domain that encodes the membrane associated or target domains. The two domains may be joined directly or linked to each other by a linking domain. The domains encoding these fusion proteins are in operational combination, i.e., operably linked, with requisite transcriptional mediation or regulatory element(s). Requisite transcriptional mediation elements that may be present in the expression module include promoters (including tissue specific promoters), enhancers, termination and polyadenylation signal elements, splicing signal elements, and the like. Of interest in some instances are inducible expression systems. The various expression constructs in the cell may be chromosomally integrated or maintained episomally, as desired. Accordingly, in some instances the expression constructs are chromosomally integrated in a cell. Alternatively, one or more of the expression constructs may be episomally maintained, as desired. The expression constructs may be expressed stably in the cell or transiently, as needed/desired.

The cells may be prepared using any convenient protocol, where the protocol may vary depending on nature of the cell, the location of the cell, e.g., in vitro or in vivo, etc. Where desired, vectors, such as plasmids or viral vectors, may be employed to engineer the cell to express the various system components, e.g., membrane-associated and target proteins, optional micro-vesicle inducer, etc., as desired. Protocols of interest include those described in published PCT application WO1999/041258, the disclosure of which protocols are herein incorporated by reference.

Depending on the nature of the cell and/or expression construct, protocols of interest may include electroporation, particle gun technology, calcium phosphate precipitation, direct microinjection, viral infection and the like. The choice of method is generally dependent on the type of cell being transformed and the circumstances under which the transformation is taking place (i.e., in vitro, ex vivo, or in vivo). A general discussion of these methods can be found in Ausubel, et al, Short Protocols in Molecular Biology, 3rd ed., Wiley & Sons, 1995. In some embodiments, lipofectamine and calcium mediated gene transfer technologies are used. After the subject nucleic acids have been introduced into a cell, the cell is may be incubated, normally at 37° C., sometimes under selection, for a period of about 1-24 hours in order to allow for the expression of the chimeric protein. In mammalian target cells, a number of viral-based expression systems may be utilized to express a chimeric protein(s). In cases where an adenovirus is used as an expression vector, the chimeric protein coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the chimeric protein in infected hosts. (e.g., see Logan & Shenk, Proc. Natl. Acad. Sci. USA 81:355-359 (1984)). The efficiency of expression may be enhanced by the inclusion of appropriate transcription enhancer elements, transcription terminators, etc. (see Bittner et al., Methods in Enzymol. 153:51-544 (1987)).

Where long-term, high-yield production of the chimeric proteins is desired stable expression protocols may be used. For example, cell lines, which stably express the chimeric protein, may be engineered. Rather than using expression vectors which contain viral origins of replication, host cells can be transformed with chimeric protein expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. In addition, the coding sequences can be inserted by means of zinc finger nucleases, meganucleases, TAL effector nucleases, or RGEN mediated methods followed by HR or homologous recombination into "safe harbor" regions of the human or other genomes. Safe harbor regions of interest include regions that are single copy, diploid or aneuploid and are not near genes that regulate growth or are likely to cause cancerous transformation or other non-therapeutic perturbations if not properly regulated.

Production of Micro-Vesicles from Micro-Vesicle Producing Cells

Aspects of the methods include maintaining a micro-vesicle producing cell, e.g., as described above, under conditions sufficient to produce one or more micro-vesicles from the cell, where the micro-vesicles include a dimerization complex of a membrane associated protein and a target protein. Any convenient methods of maintaining the cell under conditions sufficient to produce a micro-vesicle may be utilized in the subject methods. In some cases, the cell is maintained for a period of time ranging from 30 minutes to 1 week, such as from 1 hour to 3 days, 1 hour to 2 days, including 1 hour to 24 hours. In some instances, the cell is maintained for a period of time ranging from 30 minutes to 72 hours, such as 2 to 72 hours, 6 to 72 hours, 12 to 72 hours, 24 to 72 hours, 36 to 72 hours, including 48 to 72 hours. The cell may be maintained at a temperature that supports micro-vesicle production from the cell, where temperatures of interest include 4 to 42° C., such as 15 to 37° C. The cell may be maintained in a suitable culture medium, as desired, where culture media of interest include, but are not limited to: DMEM, HAMs F12, RPMI1640, serum free conditions, and the like.

Depending on the nature of the cell, aspects of the methods may include a step of inducing expression of the one or more of the membrane associated protein, the target protein and the micro-vesicle inducer, if present. Expression of one or more of these proteins may be controlled by an inducible promoter, such as an inducible promoter of a Lac-based system or a Tet-based system. In such instances, the methods may include introducing into the cell an expression inducer, e.g., by contacting the cell with a medium that includes the inducer, etc.

Where desired, aspects of the methods may include contacting a cell with a micro-vesicle inducer in a manner sufficient to cause micro-vesicle production from the cell. For example, where the micro-vesicle inducer is a small molecule inducer, the methods may include contacting the cell with a medium that includes a sufficient concentration of the micro-vesicle inducer. In some instances, micro-vesicle production may be induced by modifying the cell culture conditions of the cell, such as modifying the temperature, e.g., to a value ranging from 15 to 42° C., modifying the $Ca^{2+}$ concentration, e.g., as described in Biochemistry. 1998 Nov. 3; 37(44):15383-91, etc.

Depending on the nature of the cell, aspects of the methods may include a step of introducing into the cell a dimerization mediator. The dimerization mediator may be introduced into the cell using any convenient protocol. The particular protocol that is employed may vary, e.g., depending on whether the micro-vesicle producing cell is in vitro or in vivo. For in vitro protocols, introduction of the dimerization mediator into the cell may be achieved using any convenient protocol. In some instances, the sample includes cells that are maintained in a suitable culture medium, and the dimerization mediator is introduced into the culture medium. For in vivo protocols, any convenient administration protocol may be employed. Depending upon the binding affinity of the dimerization mediator, the response desired, the manner of administration, e.g., i.v., s.c., i.p., oral, etc., the half-life, the number of cells present, various protocols may be employed.

In some embodiments, the method further includes separating the micro-vesicle from the cell. Any convenient separation protocol may be employed. Examples of suitable separation protocols include, but are not limited to: filtration, centrifugation, precipitation, surface and/or antibody based capture and the like. In some cases, micro-vesicles are harvested from the cell supernatant post-transfection. In certain cases, the micro-vesicles may be isolated by filtration (for example on 0.45 um pore filters) of the cell supernatant of the cells according to the invention and ultracentrifugation for example, by ultracentrifugation at 110,000 g for 1.5 hours or centrifugation at 7500 g for 16 hours. In certain instances, the micro-vesicles may be frozen and stored at −80° C. without losing their ability to transfer material to the target cell. In some embodiments, the micro-vesicles do not include any nucleic acid coding for the target protein of interest. In certain embodiments, the micro-vesicles are virus free.

The amount of the target protein in the micro-vesicle may be evaluated at any convenient time during the subject methods, e.g., during the maintaining of cells step, or before or after an optional separating step, and utilizing any convenient method.

In certain embodiments, a given method only employs a single membrane associated protein/target protein pair. In yet other embodiments, given method may employ two or more distinct membrane associated/target protein pairs, such as where the production of micro-vesicles having two or more target proteins packaged therein is desired. In yet other embodiments, two or more distinct target proteins may be configured to dimerize to a common dimerization domain of membrane associated protein, such that one has a single membrane associated protein with two or more distinct target proteins.

Protein Enriched Micro-Vesicles

Aspects of the invention further include protein-enriched micro-vesicles, e.g., such as produced by the methods described above. The micro-vesicles may include one or more membrane-associated proteins and one or more target proteins, e.g., as described above, inside of a lipid bilayer envelope. As the micro-vesicles are produced from micro-vesicle producing cells, e.g., as described above, the lipid bilayer component of the micro-vesicle includes membrane components of the cell from which the micro-vesicle is produce, e.g., phospholipids, membrane proteins, etc. In addition, the micro-vesicle has a cytosol that includes components found in the cell from which the micro-vesicle is produced, e.g., solutes, proteins, nucleic acids, etc., but not all of the components of a cell, e.g., they lack a nucleus. In some embodiments, the micro-vesicles are considered to be exosome-like. The micro-vesicles may vary in size, and in some instances have a diameter ranging from 30 and 300 nm, such as from 30 and 150 nm, and including from 40 to 100 nm.

In some cases, in the micro-vesicle, the membrane-associated protein and the target protein are present in a dimerized complex. In some instances, the first and second dimerization domains are specifically bound to each other in a dimerized complex. In other instances, the first and second dimerization domains are bound to each other by a dimerization mediator, e.g., as described above. In some instances, the micro-vesicle includes a micro-vesicle inducer, e.g., a viral membrane fusion protein, such as VSV-G. In some embodiments, the first dimerization domain of the membrane-associated protein contacts the cytosol of the micro-vesicle.

A given micro-vesicle may be enriched with a single target protein or two or more distinct target proteins. Where two or more distinct target proteins are present in the micro-vesicle, each of the target proteins may dimerize with the same membrane-associated protein or each target protein may dimerize with its own membrane-associated protein, as desired. As such, in some instances a micro-vesicle may include a population of dimerized complexes that have a common membrane-associate protein but two or more distinct target proteins represented in the population. In other instances, the population of dimerized complexes may include two or more distinct target proteins each dimerized with a distinct membrane-associated protein. As such, the micro-vesicle may further include a second target protein comprising a third dimerization domain.

Micro-Vesicle Mediated Protein Delivery Into a Cell

As summarized above, aspects of the invention include methods of introducing a protein into a target cell. Such methods include contacting the target cell with a micro-vesicle, e.g., as described above, where the micro-vesicle may be present in a composition of a population of micro-vesicles (for example where the number of micro-vesicles ranges from $10^3$ to $10^{16}$, such as $10^4$ to $10^{13}$, including as $10^4$ to $10^9$), under conditions sufficient for the micro-vesicle to fuse with the target cell and deliver the target protein contained in the micro-vesicle into the cell. Any convenient protocol for contacting the cell with the micro-vesicle may be employed. The particular protocol that is employed may vary, e.g., depending on whether the target cell is in vitro or in vivo. For in vitro protocols, target cells may be maintained with micro-vesicles in a suitable culture medium under conditions sufficient for the micro-vesicles to fuse with the target cells. Examples of suitable culture media include, but are not limited to: DMEM, Hams F12, RPMI1640 and the like. The target cells and micro-vesicles may be maintained for a period of time sufficient for the micro-vesicles to fuse with the cells, where the period of time ranges, in some instances, from 5 mins to 72 hrs, such as 30 mins to 2 hrs. The target cells and micro-vesicles may be maintained at a suitable temperature, e.g., a temperature ranging from 4° C. to 42° C., such as 15° C. to 37° C. For in vivo protocols, any convenient administration protocol may be employed. Depending upon the tropism of the micro-vesicle and the target cell, the response desired, the manner of administration, e.g. i.v., s.c., i.p., oral, etc., the half-life, the number of cells present, various protocols may be employed.

In some embodiments, the method further includes disrupting (i.e., dissociating) the dimerized complex in the micro-vesicle. Dissociation of the dimerized complex may lead to faster release of the target protein in the cell resulting in a faster and or larger biological response in the cell. The dimerized complex may be disrupted using any convenient protocol. In some embodiments, the method may include contacting the micro-vesicle with a solubilizer, i.e., dimerization disruptor, compound to dissociate the complex of the target protein and the membrane-associated protein in the micro-vesicle. Any convenient solubilizer compounds may be utilized. Solubilizer compounds of interest include, but are not limited to, the D/D solubilizer compound (Clontech, Mountain View, Calif.). The D/D solubilizer may dissociate dimeric complexes that include DmrD dimerization domains, by binding to the DmrD domain in a manner that disrupts (reverses) their self-association. The D/D solubilizer also dissociates complexes that include the DmrB homodimerization domain.

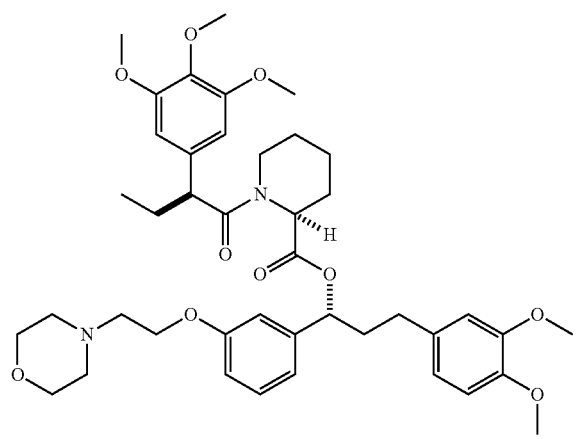

Structure of D/D Solubilizer

In those instances where the dimerization complex includes a dimerization mediator, excess mediator may be introduced into the micro-vesicles, e.g., as described above, in order to dissociate the complex. Where the dimerization mediator is a modifiable dimerization mediator, dissociation of the complex may include applying a stimulus to the micro-vesicle to modify a modifiable dimerization mediator to dissociate the dimeric complex of target protein and membrane-associated protein. In such embodiments, the target cells may be maintained for any convenient period of time prior to application of a stimulus, such as a photon, a chemical agent or an enzyme, to the cells. As such, further aspects of embodiments of the method include application of a stimulus to a sample that includes the target cells and the micro-vesicles to modify the modifiable dimerization domain and disrupt dimerization complex of the membrane-associated protein and the target protein, respectively.

In certain instances, the method further includes assessing, i.e., evaluating, a function of the target protein in the cell. Once the target protein of interest has been introduced into a target cell, the occurrence of a particular biological event triggered by the introduction of the target protein into the cell may be evaluated. Evaluation of the cells may be performed using any convenient method, and at any convenient time before, during and/or after contact of the micro-vesicles with the cells. Evaluation of the cells may be performed continuously, or by sampling at one or more time points during the subject method. In some embodiments, the evaluating step is performed prior to the contacting step. In certain embodiments, the evaluating step is performed prior to application of a stimulus. In certain cases, the evaluation is performed using a cell-based assay that measures the occurrence of a biological event triggered by the target protein. Any observable biological property of interest may be used in the evaluating steps of the subject methods.

Embodiments of the methods are characterized by providing for transient activity of the delivered protein in the target cell. By transient is meant that the delivered protein remains active for a limited period of time, and in some embodiments the limited period of time ranges from 10 min to 96 hr, including 2 hr to 48 hr. It yet other embodiments, the protein may remain active for longer period of time, e.g., 96 hr or longer, such as 100 hr or longer, including 200 hr or longer.

Utility

The micro-vesicles, cells and methods of the invention, e.g., as described above, find use in a variety of applications where the introduction of a protein or proteins of interest into a target cell is of interest. Applications of interest include, but are not limited to: research applications, diagnostic applications and therapeutic applications. Accordingly, target proteins that may be delivered using methods of the invention include research proteins, diagnostic proteins and therapeutic proteins.

Research proteins are proteins whose activity finds use in a research protocol. As such, research proteins are proteins that are employed in an experimental procedure. The research protein may be any protein that has such utility, where in some instances the research protein is a protein domain that is also provided in research protocols by expressing it in a cell from an encoding vector. Examples of specific types of research proteins include, but are not limited to: transcription modulators of inducible expression systems, members of signal production systems, e.g., enzymes and substrates thereof, hormones, prohormones, proteases, enzyme activity modulators, perturbimers and peptide aptamers, antibodies, modulators of protein-protein interactions, genomic modification proteins, such as CRE recombinase, meganucleases, Zinc-finger nucleases, CRISPR/Cas-9 nuclease, TAL effector nucleases, etc., cellular reprogramming proteins, such as Oct 3/4, Sox2, Klf4, c-Myc, Nanog, Lin-28, etc., and the like.

Diagnostic proteins are proteins whose activity finds use in a diagnostic protocol. As such, diagnostic proteins are proteins that are employed in a diagnostic procedure. The diagnostic protein may be any protein that has such utility. Examples of specific types of diagnostic proteins include, but are not limited to: members of signal production systems, e.g., enzymes and substrates thereof, labeled binding members, e.g., labeled antibodies and binding fragments thereof, peptide aptamers and the like.

Proteins of interest further include therapeutic proteins. Therapeutic proteins of interest include without limitation, hormones and growth and differentiation factors including, without limitation, insulin, glucagon, growth hormone (GH), parathyroid hormone (PTH), growth hormone releasing factor (GHRF), follicle stimulating hormone (FSH), luteinizing hormone (LH), human chorionic gonadotropin (hCG), vascular endothelial growth factor (VEGF), angioproteinetins, angiostatin, granulocyte colony stimulating factor (GCSF), erythroproteinetin (EPO), connective tissue growth factor (CTGF), basic fibroblast growth factor (bFGF), acidic fibroblast growth factor (aFGF), epidermal growth factor (EGF), transforming growth factor .alpha. (TGFα), platelet-derived growth factor (PDGF), insulin growth factors I and II (IGF-I and IGF-II), any one of the transforming growth factor β-superfamily, including TGFβ, activins, inhibins, or any of the bone morphogenic proteins (BMP) including BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Proteins of interest further include, but are not limited to: fibrinolytic proteins, including without limitation, urokinase-type plasminogen activator (u-PA), and tissue plasminogen activator (tpA); procoagulant proteins, such as Factor Vila, Factor VIII, Factor IX and fibrinogen; plasminogen activator inhibitor-1 (PAI-1), von Willebrand factor, Factor V, ADAMTS-13 and plasminogen for use in altering the hemostatic balance at sites of thrombosis; etc.

Also of interest as proteins are transcription factors such as jun, fos, max, mad, serum response factor (SRF), AP-1, AP2, myb, MyoD, myogenin, ETS-box containing proteins, TFE3, E2F, ATF1, ATF2, ATF3, ATF4, ZF5, NFAT, CREB, HNF4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Also of interest as proteins are carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

Target cells to which proteins may be delivered in accordance with the invention may vary widely. Target cells of interest include, but are not limited to: cell lines, HeLa, HEK, CHO, 293 and the like, Mouse embryonic stem cells, human stem cells, mesenchymal stem cells, primary cells, tissue samples and the like Kits Aspects of the invention further include kits, where the kits include one or more components employed in methods of making protein enriched microvesicles, e.g., as described above. In some instances, the kits may include genetic constructs which can be used to make a micro-vesicle producing cell. Such genetic constructs may include a coding sequence for the membrane-associated protein, e.g., as described above, where the coding sequence may be present in an expression cassette, where the promoter of the expression cassette may or may not be inducible. Genetic constructs present in the kit may include a coding sequence for the target protein, e.g., as described above, where the coding sequence may be present in an expression cassette, where the promoter of the expression cassette may or may not be inducible. In yet other embodiments, the genetic construct provided in the kit may be an expression cassette configured to receive a coding sequence for a target protein, but that lacks the target protein coding sequence. For example, the genetic construct may include a promoter separated from a dimerization domain by a restriction site (e.g., a multiple cloning site). Genetic constructs present in the kit may include a coding sequence for the micro-vesicle inducer, e.g., as described above, where the coding sequence may be present in an expression cassette, where the promoter of the expression cassette may or may not be inducible. The genetic constructs may be present on separate vectors, as desired, or may be combined onto a single vector, where vectors of interest include, but are not limited, plasmids, viral vectors, etc. In some instances, the kits include micro-vesicle producing cells, e.g., as described above. Where desired, the kits may include additional reagents, such as micro-vesicle inducers, dimerization mediators, dimerization disrupters, etc. The various components of the kits may be present in separate containers, or some or all of them may be pre-combined into a reagent mixture in a single container, as desired. Kits may also include a quantity of control microvesicles expressing a detectable protein (e.g., AcGFP, etc) as a control. Where desired, the kits may also include antibodies for detecting the microvesicles, substrates for quantifying microvesicle containing reporter proteins like luciferase or tranasfection reagents or purification systems or kits for purifying of concentrating the microvesicles.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), portable flash drive, Hard Drive etc., on which the information has been recorded. Yet another form of these instructions that may be present is a website address which may be used via the internet to access the information at a removed site.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Example I

Directed packaging of a protein was tested by creating a matched pair of binding partners utilizing the ligand-inducible heterodimerization domains contained in the iDimerize System (Clontech, Mountain View, Calif.). The binding partners consisted of the CherryPicker protein (a membrane-targeted red fluorescent protein) fused to two DmrA domains and the CRE recombinase enzyme fused to a single DmrC domain, as illustrated in FIG. 2A. The CherryPicker and CRE expression plasmids were co-transfected with a VSV-G expression plasmid into 293T cells as illustrated in FIG. 1 and allowed to incubate for 48-72 hours to produce microvesicles either in the presence or absence of the A/C heterodimerizer.

Micro-vesicles were collected and assayed for relative CRE protein amount by Western blot using an anti-DmrC antibody.

Figure 2C:
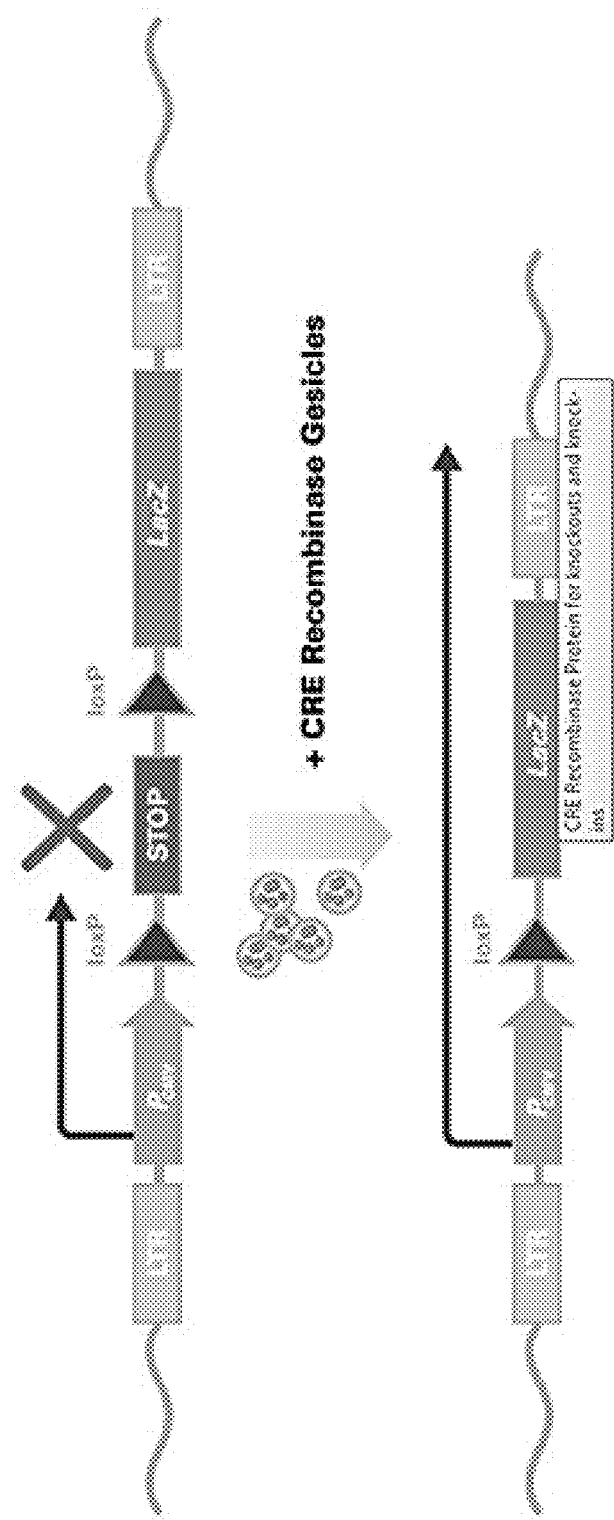

In addition, micro-vesicles were also assayed for CRE activity in a cell-based assay. CRE micro-vesicles were added to a cell line that required CRE to express a LacZ marker through removal of a stop cassette flanked by IoxP sites. CRE Recombinase microvesicles, when applied to target cells, fuse with the plasma membrane and discharge CRE Recombinase into the cell, as illustrated in FIG. 2B. CRE Recombinase is transported to the nucleus via a nuclear localization signal where it can carry out CRE-mediated recombination between LoxP sites, as illustrated in FIG. 2C. CRE Recombinase microvesicles are labeled with the CherryPicker (Clontech, Mountain View, Calif.) so that treated target cells can be easily visualized by fluorescent microscopy.

Western analysis showed that more CRE enzyme was present in the micro-vesicles produced in the presence of A/C heterodimerizer than without. Cell based analysis demonstrated that the A/C heterodimerizer was a requirement to deliver enough CRE to induce LacZ expression in the target cells.

Figure 2D:
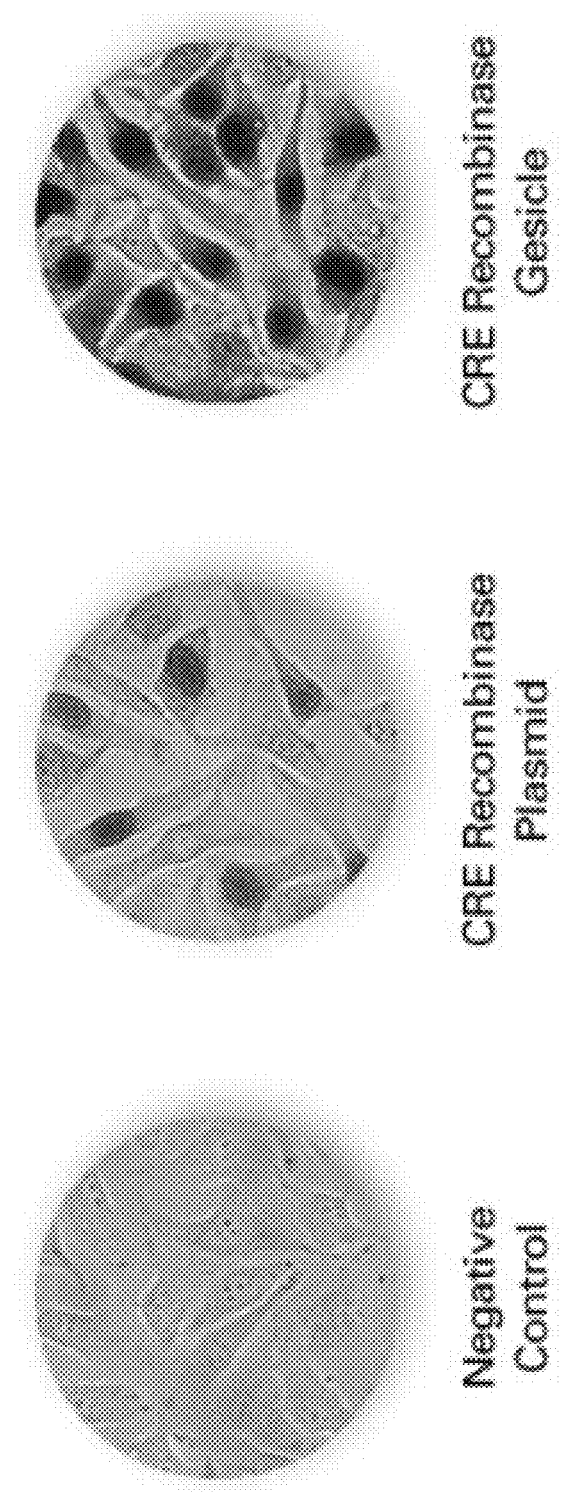
Figure 3:
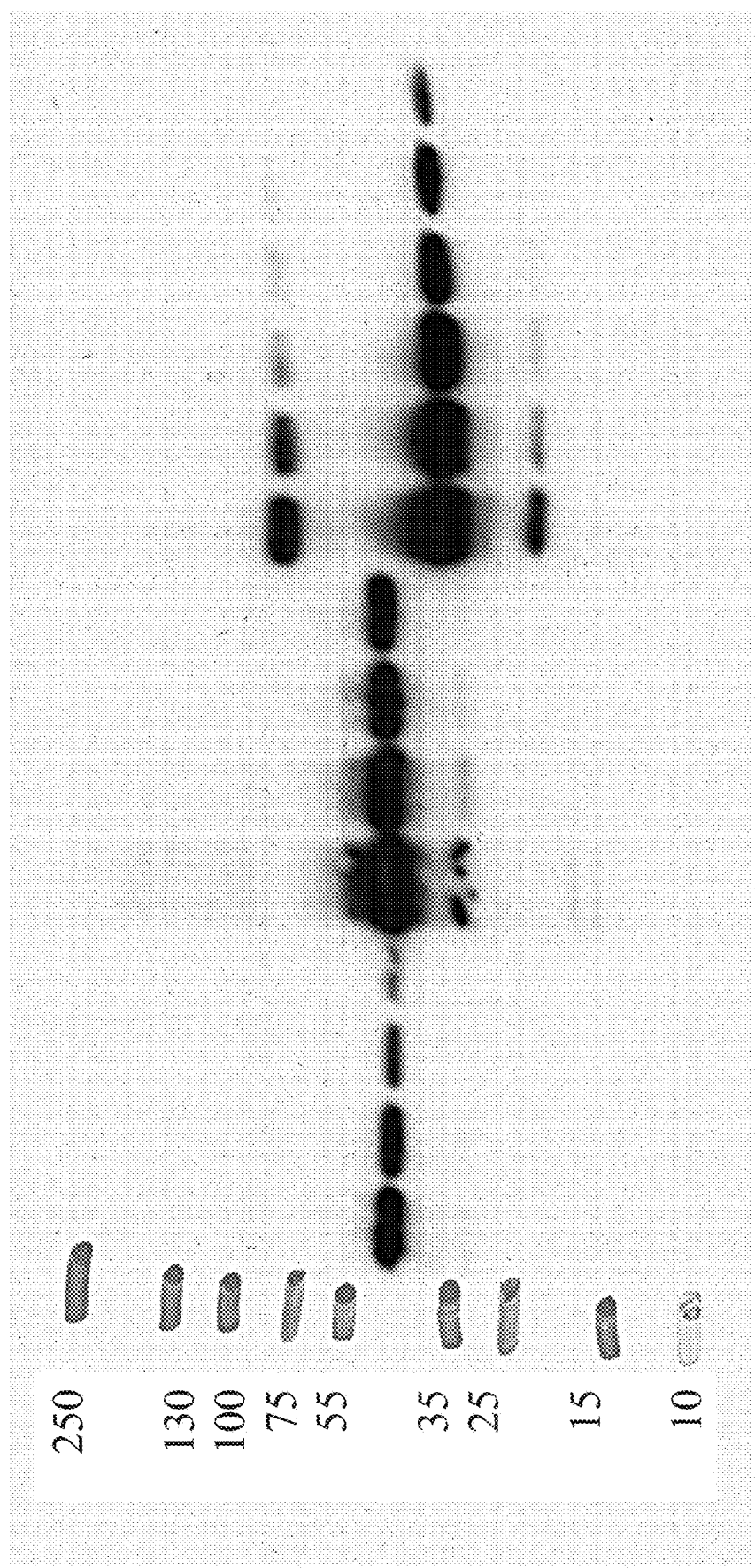
FIG. 3 provides the results of assay of micro-vesicle target protein content.

Rapid and efficient genome modification using CRE Recombinase Gesicles is also shown in FIG. 2D. A cell line harboring an integrated, IoxP-conditional LacZ expression cassette was either transfected for 6 hr with a plasmid expressing CRE recombinase (middle image) or treated with 20 μl CRE Recombinase-containing microvesicles for 3 hr (right image). 24 hr after treatment, cells were stained for LacZ expression using the Beta-Galactosidase Staining Kit from Clontech (Cat. No. 631780). The Beta Galactosidase gene is only expressed when the upstream IoxP-flanked stop codon is excised by CRE Recombinase. Results showed that, compared to plasmid transfection delivery of CRE Recombinase, using microvesicles resulted in faster and more efficient excision Example II Ligand dependent enrichment into gesicles has been shown for cytoplasmic proteins (Example: cytosolic AcGFP) yielding an 8 to 10 fold increase of target protein packaging efficiency into the gesicles. CherryPicker and AcGFP expression plasmids were co-transfected with a VSV-G expression plasmid into 293T cells to produce micro-vesicles either in the presence or absence of the A/C heterodimerizer. Micro-vesicles were collected and assayed for relative AcGFP protein amount by Western blot using an anti-DmrC antibody. Densitometric analysis of bands of similar intensity revealed that packaging of the AcGFP in the presence of the A/C heterodimerizer was 8-10-fold more efficient than packaging without the A/C heterodimerizer. The results are shown in FIG. 3 and provided in the Table 1 below:

TABLE 1

| | Sample | Amount |
|---|---|---|
| 1 | DmrC AcGFP microvesicle (−) | 5 uL |
| 2 | DmrC AcGFP microvesicle (−) | 2.5 uL |
| 3 | DmrC AcGFP microvesicle (−) | 1.25 uL |
| 4 | DmrC AcGFP microvesicle (−) | 0.625 uL |
| 5 | DmrC AcGFP microvesicle (+) | 5 uL |
| 6 | DmrC AcGFP microvesicle (+) | 2.5 uL |
| 7 | DmrC AcGFP microvesicle (+) | 1.25 uL |
| 8 | DmrC AcGFP microvesicle (+) | 0.625 uL |
| 9 | rAcGFP | 25 ng |
| 10 | rAcGFP | 12.5 ng |
| 11 | rAcGFP | 6.25 ng |
| 12 | rAcGFP | 3.125 ng |
| 13 | rAcGFP | 1.56 ng |
| 14 | rAcGFP | 0.78 ng |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A micro-vesicle comprising:
 a membrane-associated chimeric protein comprising a first dimerization domain; and
 a target chimeric protein that is not membrane-associated comprising a second dimerization domain,
 wherein the first and second dimerization domains are specifically bound to each other in a dimerized complex or the first and second dimerization domains are bound to each other by a single dimerization mediator.

2. The micro-vesicle according to claim 1, wherein the first and second dimerization domains are specifically bound to each other in the dimerized complex.

3. The micro-vesicle according to claim 1, wherein first and second dimerization domains are bound to each other by a single dimerization mediator.

4. The micro-vesicle according to claim 3, wherein the dimerization mediator is a modifiable dimerization mediator.

5. The micro-vesicle according to claim 1, wherein the micro-vesicle further comprises a micro-vesicle inducer.

6. The micro-vesicle according to claim 5, wherein the micro-vesicle inducer comprises a viral membrane fusion protein.

7. The micro-vesicle according to claim 6, wherein the viral membrane fusion protein is VSV-G.

8. The micro-vesicle according to claim 1, wherein the membrane-associated chimeric protein is selected from the group consisting of a myristoylated protein, a farnesylated protein, a membrane anchor protein, a transmembrane protein and membrane lipid protein.

9. The micro-vesicle according to claim 1, wherein the first and second dimerization domains are heterodimeric.

10. The micro-vesicle according to claim 1, wherein the first and second dimerization domains are homodimeric.

11. The micro-vesicle according to claim 1, wherein the first and second dimerization domains are selected from DmrA and DmrC domains, DmrB domains, DmrD domains, dimerization domains of the dihydrofolate reductase system, dimerization domains of TAg and p53, and dimerization domains of Src Homology 2 and a phosphotyrosine-binding protein.

12. The micro-vesicle according to claim 1, wherein the micro-vesicle further comprises a second target protein comprising a third dimerization domain.

13. The micro-vesicle according to claim 1, wherein the target chimeric protein is a research protein selected from the group consisting of: a genomic modification protein, a transcription modulator of an inducible expression system, a member of a signal production system, a hormone, a pro-hormone, a protease, an enzyme activity modulator, a peptide aptamer, an antibody, a modulator of a protein-protein interaction, and a cellular reprogramming protein.

14. The micro-vesicle according to claim 13, wherein the research protein is a genomic modification protein.

15. The micro-vesicle according to claim 14, wherein the genomic modification protein is selected from the group consisting of: a CRE recombinase, a meganuclease, a Zinc-finger nuclease, a clustered regularly interspaced short palindromic repeats/CRISPER associated protein 9 (CRISPR/Cas-9) nuclease and a transcription activator-like (TAL) effector nuclease.

16. The micro-vesicle according to claim 1, wherein the membrane associated with the membrane-associated protein is separate from a cell.

\* \* \* \* \*